United States Patent [19]
Fujimori

[11] Patent Number: 6,161,449
[45] Date of Patent: Dec. 19, 2000

[54] STEERING WHEEL ROTATING APPARATUS FOR PHYSICALLY HANDICAPPED PERSONS

[76] Inventor: Yoshio Fujimori, 25-22-809 Mure 6-chome, Mitaka-shi, Tokyo, Japan

[21] Appl. No.: 09/363,854

[22] Filed: Jul. 30, 1999

[30] Foreign Application Priority Data

Aug. 27, 1998 [JP] Japan ................................. 10-257589

[51] Int. Cl.[7] .................................................... B62D 1/04
[52] U.S. Cl. ............................................................ 74/557
[58] Field of Search ........................... 74/557, 553, 552; D12/177

[56] References Cited

U.S. PATENT DOCUMENTS

| | | | |
|---|---|---|---|
| 2,228,393 | 1/1941 | Leaming | 74/557 |
| 5,289,736 | 3/1994 | Fujimori | 74/557 |
| 5,520,071 | 5/1996 | Jones | 74/557 |

FOREIGN PATENT DOCUMENTS 59-36518  10/1984  Japan.

*Primary Examiner*—Mary Ann Green
*Attorney, Agent, or Firm*—Leydig, Voit & Mayer, Ltd.

[57] ABSTRACT

A steering wheel rotating apparatus for physically handicapped persons includes a grip holder having a grip hole and an engaging member projectable from the inside surface of the grip hole. The grip holder is fixed to the steering wheel of an automobile. A rotary grip having a shaft with an insertion part is detachably received in the grip hole and a grip body part mounted on the shaft, and a switch unit having a switch case and switches is detachably fitted to the grip holder, so that a physically handicapped person may operate the steering wheel using the rotary grip and also operate the switches by the hand which is gripping the rotary grip. When a non-physically handicapped person is to operate the steering wheel, the rotary grip and the switch unit may be removed so as not to interfere with steering wheel operation.

2 Claims, 6 Drawing Sheets

STEERING WHEEL ROTATING APPARATUS FOR PHYSICALLY HANDICAPPED PERSONS

BACKGROUND OF THE INVENTION

1. Field of the Invention

This invention relates to a steering wheel rotating apparatus to be used by physically handicapped persons in operating automobiles and more particularly to a steering wheel rotating apparatus with switches so that persons physically handicapped in one hand or persons physically handicapped in the lower limbs can operate the steering wheel and the switches for the horn, turning signal (winker), light, wiper and so on with one normal hand when the brake and accelerator are manually operated.

2. Description of the Prior Art

Generally, as the accelerator and brake of an automobile are operated with a right foot, a person physically handicapped in the lower limbs cannot operate the brake and accelerator.

Therefore, various automobile operating apparatus for physically handicapped persons have been proposed so that the accelerator and brake may be manually operated.

Figure 9:
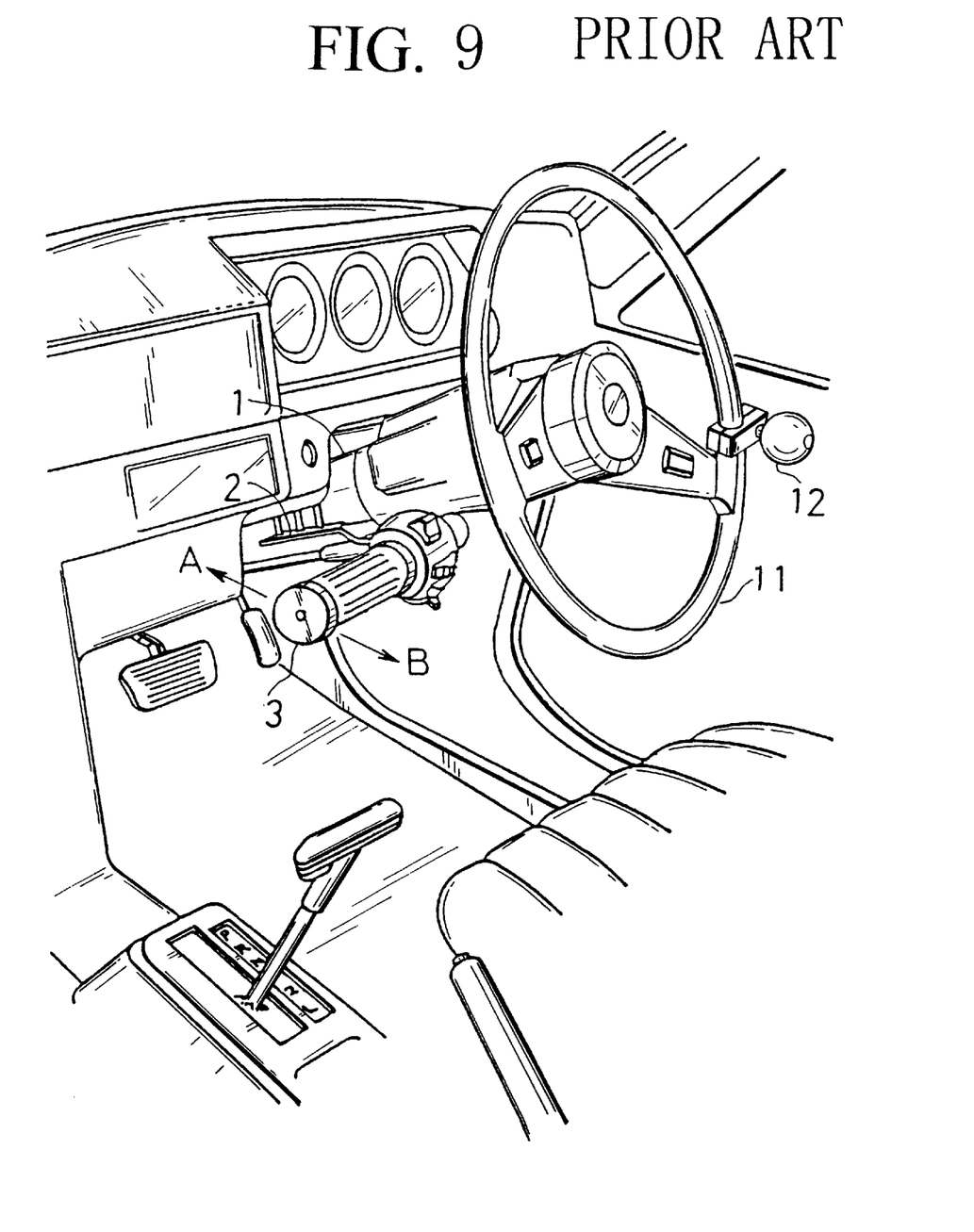
FIG. 9 is a perspective view of a conventional automobile operating apparatus for physically handicapped persons as seen from above the driver's seat.

For example, in FIG. 9 is shown an automobile apparatus for physically handicapped person suggested by the present applicant in Japanese Utility Model Application Publication No. 36518/1984. In this apparatus, a lever fitting plate 2 is fitted to a steering column 1 and a brake and accelerator operating lever 3 is pivoted on the left side of the lever fitting plate 2 and is operatively connected with a brake and accelerator apparatus. When the operating lever 3 is pushed in as shown by arrow A, the brake will be operated, and when the operating lever is pulled out as shown by arrow B, the accelerator will be operated. In such an apparatus, when the brake and accelerator are to be operated, they have to be operated with one hand (the left hand in this case) and the steering wheel will have to be operated with the only other hand (the right hand in this case). Therefore, a rotary knob 12 is fitted on the right side of the steering wheel 11 so that the steering wheel may be operated by gripping the knob with the right hand.

Further, in the same way, a person physically handicapped in one hand can operate the steering wheel by a rotary knob 12 fitted the same. In this case, a brake and an accelerator can be operated by the right foot as usually.

In the above-mentioned automobile operating apparatus for persons physically handicapped in the lower limbs, the steering wheel can be operated with one hand using the rotary knob fitted on the right side (or left side) of the steering wheel.

However, if a non-handicapped person is to ordinarily operate the steering wheel and the gripping part of the rotary knob remains fitted to the steering wheel, interference with steering wheel operation, such as catching of the sleeve end of a suit, will likely occur.

And, there is a problem which needed skill for doing various switch operations while maintaining accelerator operation to keep the automobile speed suitably, so far as switches for the horn, the turning signal, the light, the wiper or the like are arranged near the brake and the accelerator operation lever. It will be considered that said switches may be arranged near the rotary knob, however, another problem occurs when a non-handicapped person tends to touch the switches by mistake when operating the automobile.

Furthermore, in the case of a person physically handicapped in one hand, there are other problems that switch operation such as the horn, the turning signal, the light, the wiper and so on must be done with a hand being detached from the steering wheel temporarily, thus it is dangerous at the time of turning operation of the automobile.

U.S. Pat. No. 5,289,736 shows another prior art of a steering wheel rotating apparatus for physically handicapped persons. The prior art structure is provided with a grip holder with a horn switch. But the switch can not be detached, and a non-handicapped person tends to touch the switch by mistake when the operating the automobile.

SUMMARY OF THE INVENTION

A first object of the present invention is to provide a steering wheel rotating apparatus for physically handicapped persons, wherein the steering wheel and the switch operation such as the horn, the turning signal, the light, the wiper and so on can be easily operated with one hand by a physically handicapped person who manually operates the accelerator and brake apparatus, and further wherein the gripping part of the rotary knob and the switch unit can be removed easily if a non-handicapped person is to ordinarily operate the automobile in order not to interfere with steering wheel operation.

A second object of the present invention is to provide a steering wheel rotating apparatus for physically handicapped persons, wherein at least one switch is arranged on the switch unit removably fitted to the grip holder and the switch can be operated with such as a thumb etc. of the one hand gripping the rotary grip so that the switch can be operated more easily.

According to the present invention, there is provided a steering wheel rotating apparatus for physically handicapped persons comprising: a grip holder having a grip hole formed therein and means for attaching the grip holder to a steering wheel of an automobile; a rotary grip having a shaft with an insertion part being detachably received in the grip hole and a grip body part mounted on the shaft, the shaft having a partly narrowed engaging portion in the insertion part; an engaging member supported by the grip holder and having an movable portion supported for movement between a first position in which the movable portion projects into the grip hole and engages with the engaging portion of the shaft and prevents the shaft from being removed from the grip hole and second position in which the movable portion is disengaged from the engaging portion, biasing means biasing the movable portion of the engaging member toward the first position, and an operating portion for moving the movable portion between its first and second positions; a switch unit detachably fitted to the grip holder and having a switch case and at least one switch provided thereon.

BRIEF DESCRIPTION OF THE DRAWINGS

The above described object and other objects as well as new features of the present invention will now be clarified with reference to the following description and drawings. Embodiments of the present invention are exemplified in these descriptions and drawing but it is apparent that various modifications can be made within the scope of the claims.

DETAILED DESCRIPTION OF PREFERRED EMBODIMENTS

A embodiment of the present invention is shown in FIGS. 1 to 6, in which the reference numeral 20 represents a plastic grip holder fixed on a steering wheel 11 of an automobile, 40 represents a rotary grip detachably fitted to the grip holder 20, which is used in the operation of the steering wheel, 50 represents a switch unit detachably fitted to the grip holder 20.

Figure 5:
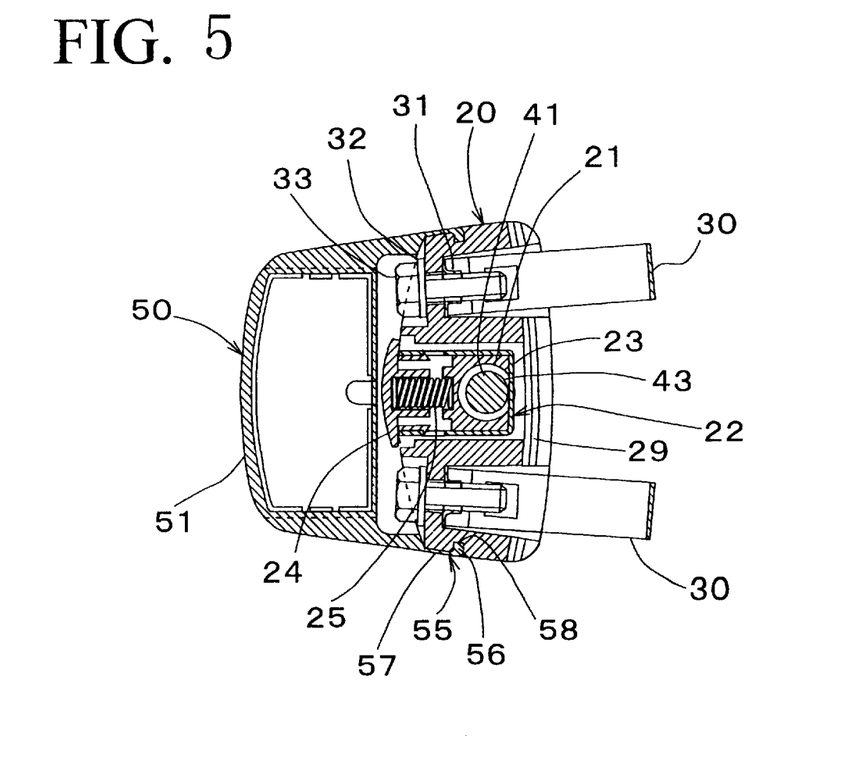
FIG. 5 is a plan sectional view of the embodiment.
Figure 6:
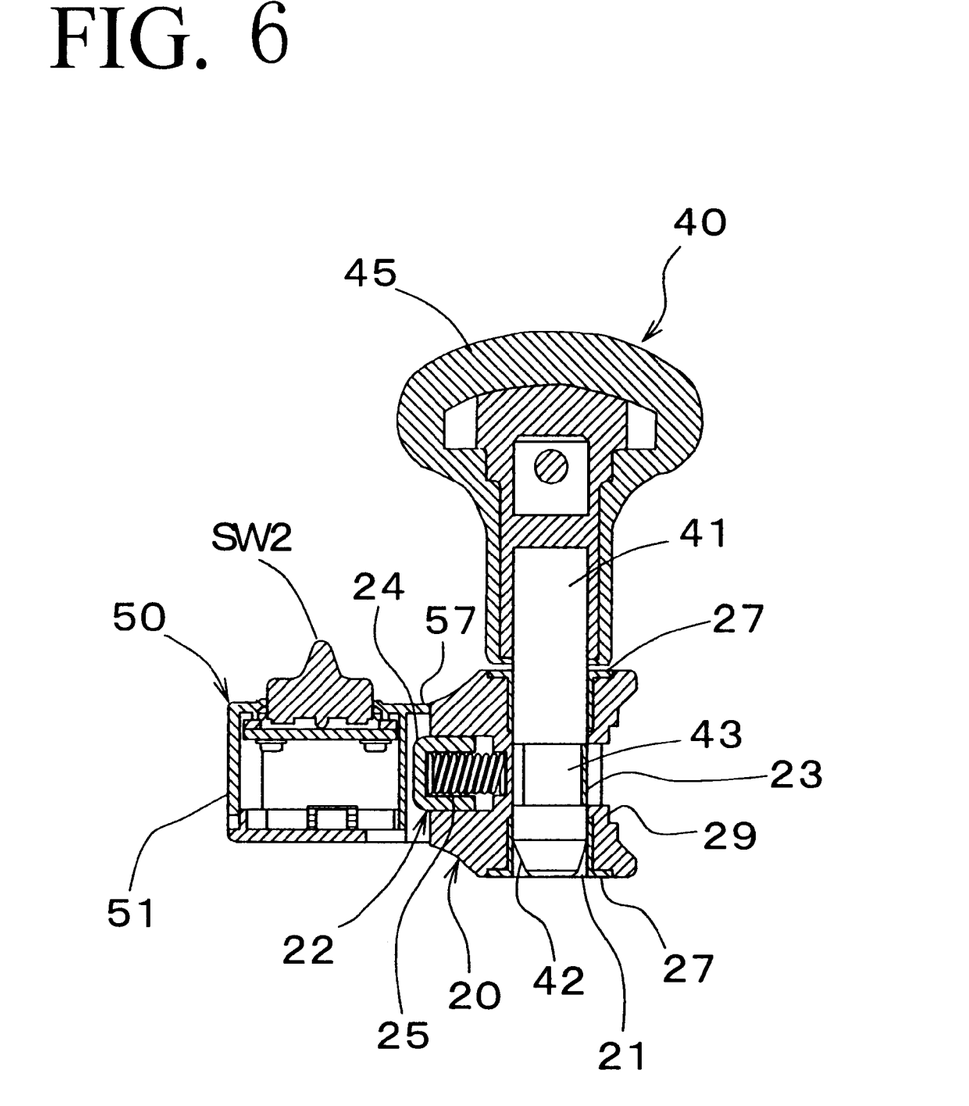
FIG. 6 is a side sectional view of the embodiment.

As shown in FIGS. 5 and 6, the grip holder 20 is provided with a grip hole 21 in the form of a circular through hole, and is fitted with an engaging member 22 so as to engage a rotary grip 40. The engaging member 22 has an engaging portion (movable portion) 23 projectable into the inside surface of the grip hole 21 and movable in the grip holder 20, and has a push button 24 as an operating portion integrally connected with the engaging portion 23. The engaging portion 23 may be a U-shaped folded metallic plate, with which the resinous push button 24 is fitted and unified. The push button 24 is engaged by the spring 25 as a biasing means so as to project from the surface of the inner periphery (the center side surface) of the grip holder 20, the surface of the inner periphery faces the center of the steering wheel 11. When the push button 24 is projecting, the engaging portion 23 partly projects into the grip hole (engaging condition). The inner surface of the grip hole 21 is reinforced by a metal bushing 27 unified with the grip holder 20 as shown in FIG. 6.

Figure 3:
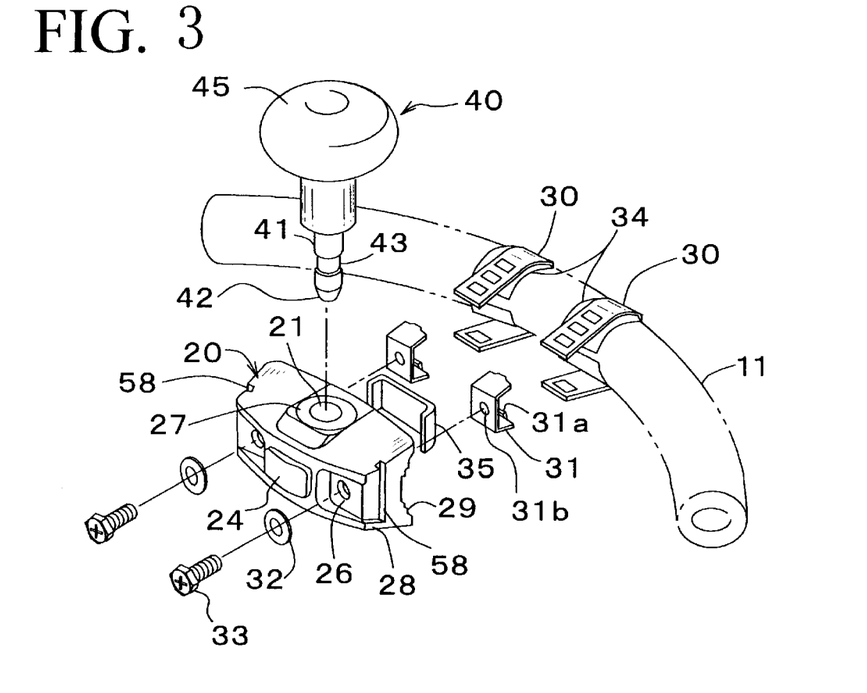
FIG. 3 is a exploded perspective view showing means for attaching the grip holder of the embodiment.
Figure 4:
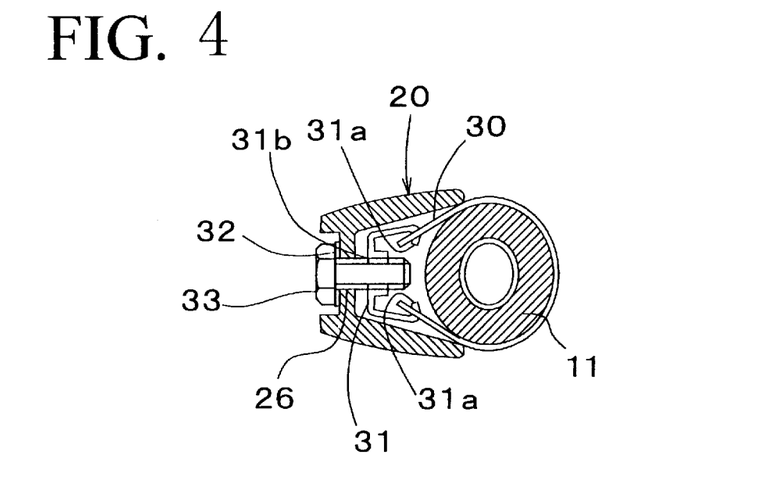
FIG. 4 is a side sectional view showing the grip holder attached to the steering wheel of the embodiment.

The grip holder 20 is curved so as to contact the inner periphery of the steering wheel 11 of the automobiles, and has step-like recesses 29, as shown in FIG. 6, on the outer peripheral surface in contact with the steering wheel to prevent the grip holder 20 from slipping and being displaced when it is fitted on the steering wheel 11. In order to fit the grip holder 20 to the steering wheel 11, through holes 26 for fixing are bored from the inner periphery to the outer periphery of the grip holder in both sides of the grip hole 21 as shown in FIGS. 3 and 4. Metallic fixing bands 30 having holes in both ends, clips 31 having picks 31a at both ends and screw holes 31b bored in the center, washers 32, and bolts 33 in the screw holes 31b are used in attaching the grip holder 20, and said picks 31a at both ends of the clips 31 are hooked with the holes of the fixing bands 30. When the surface of the steering wheel 11 is made of soft materials, elastic sheets 34, rubber for example, are interposed between the steering wheel 11 and the fixing bands 30, and also a back cover 35 may cover the outer peripheral surface of the grip holder 20.

In order to fix the grip holder 20 to the steering wheel 11, the fixing bands 30 are wound on the steering wheel 11 so that the rotary grip 40 is on the near side (in the position of the intermediate height of the steering wheel in the straight ahead state), the picks 31a at both ends of the clips 31 are hooked with the holes in the both ends of the fixing bands 30 as shown in FIG. 4, bolts 33 with washers 32 are inserted in the through holes 26 from the center side of the grip holder 20 and screwed in the screw holes 31b of the clips 31 so as to secure and clamp the band 30 on the steering wheel. The grip holder 20 will be fixed on the right side or the left side of the steering wheel 11.

Figure 1:
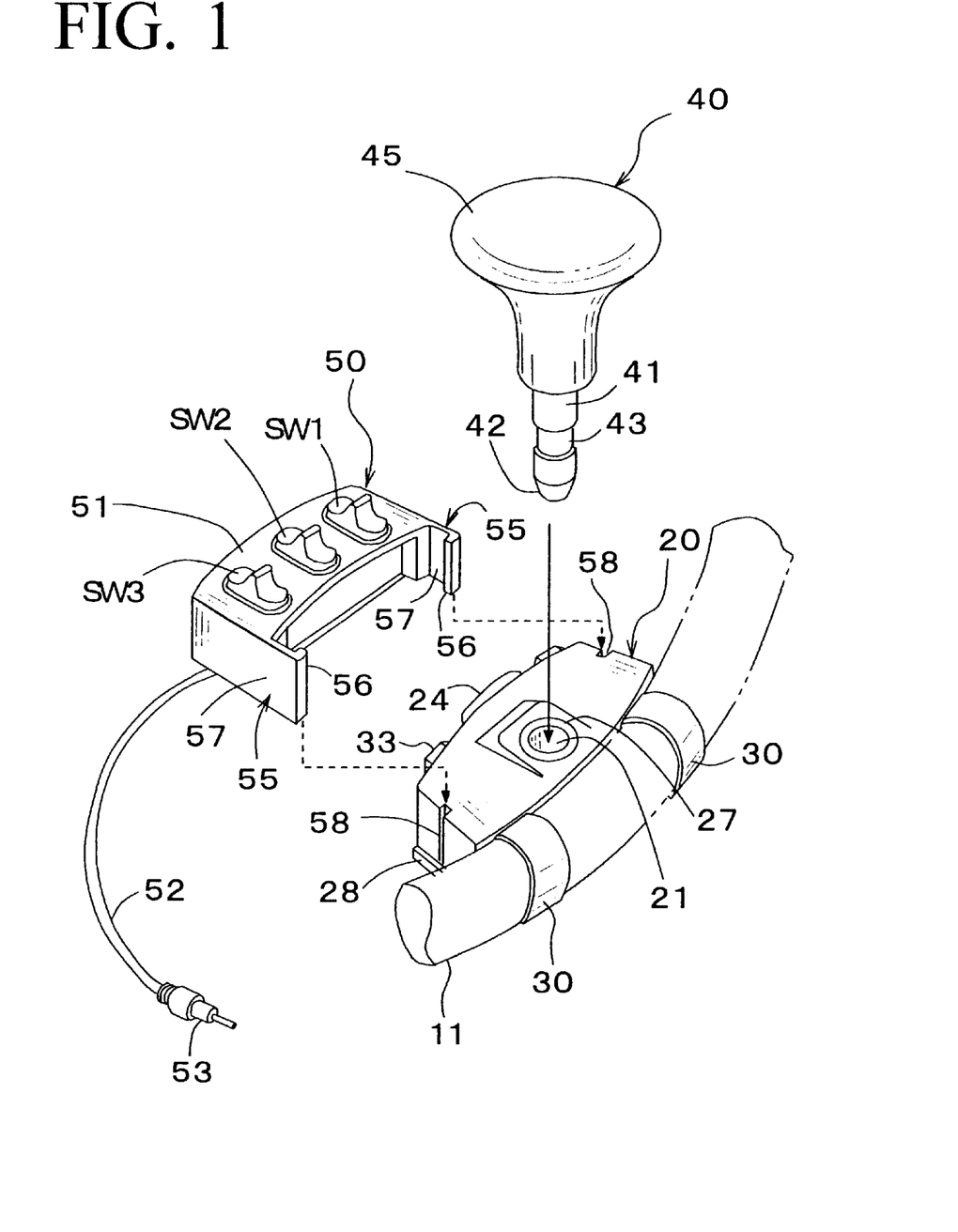
FIG. 1 is a exploded perspective view showing an embodiment of a steering wheel rotating apparatus for physically handicapped persons according to the present invention.
Figure 2:
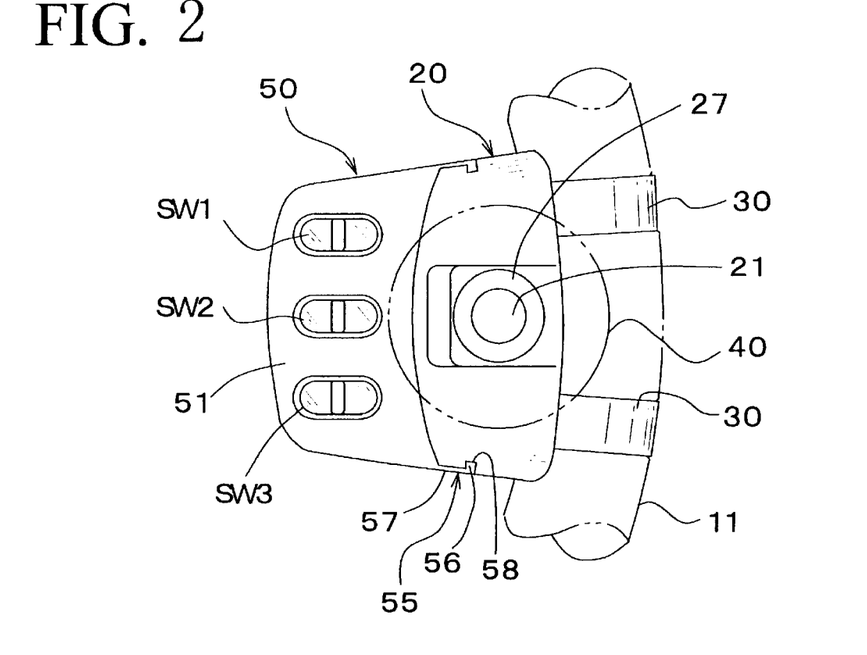
FIG. 2 is a plan view of the embodiment.

As shown in FIGS. 1, 3 and 6, the rotary grip 40 includes a metallic shaft 41 that can be freely fitted into the grip hole 21 of the grip holder 20 and a grip body part 45 mounted integrally (unified) on the shaft 41. The shaft 41 has the shape of a column so as to be fitted rotatably into the grip hole 21 (inner peripheral of the metal bush 27) without play, and its tip has a taper 42 so as to be easily fitted into the grip hole 21. In the insertion part of the shaft 41 in contact with the engaging portion 23 of the engaging member 22 projecting on the inside surface of the grip hole 21 when the shaft 41 is fitted into the grip hole 21, there is provided a partly narrowed engaging portion 43 being a narrower column shape than other parts of the shaft 41.

Next, the method of attaching and detaching the rotary grip 40 the grip holder 20 will be explained. In removing the rotary grip 40 fitted to the grip holder 20, first of all, the push button 24 of the engaging member 22 for the rotary grip is pushed, so that the engaging portion 23 engaged with the engaging portion 43 of the shaft 41 will retract from the inside surface of the grip hole 21 (to the second position of the engaging portion 23), and when the rotary grip 40 is lifted, it can be removed from the grip hole 21. In fitting the rotary grip 40 to the grip holder 20, when the shaft 41 of the rotary grip 40 is fitted and pushed into the grip hole 21, the engaging portion 23 of the engaging member 22 is moved back by the taper 42 of the shaft 41 in spite of the elasticity of the spring 25, and the shaft 41 is inserted deeply. And when the engaging portion 43 of the shaft is opposite to the engaging portion 23, the engaging portion 23 engaged by the elasticity of the spring 25 so as to project from the inside surface of the grip hole 21 and engage the engaging portion 43. Thus, the shaft 41, in this state (the first position of the engaging portion 23), cannot be pulled out.

In the switch unit 50 a horn switch SW1, a turning signal switch (winker switch) SW2, a light switch SW3 are provided on a switch case 51 which is made of resin, etc. The horn switch SW1 is a switch which is ON only in operation for example, the turning signal switch SW2 is a changeover switch for the signal of left-turn and right-turn of an automobile, the light switch SW3 is a changeover switch for ON-OFF of a head light and a width indicator light of an automobile. In order to control the horn, the turning signal and the light, an electrical circuit is provided on the steering column. A harness 52 for electric wiring is connected to these switches SW1, SW2, SW3 on the switch case 51, and the harness 52 is to be connected to the electrical circuit through a connector 53. Moreover, the horn switch SW1, the turning signal switch SW2 and the light switch SW3 are all arranged at the position so as to be operated by a driver's hand which also holds the rotary grip 40 at the same time (the position operatable by the thumb of the hand etc., for example), and said switches attached on the upper surface of the switch case 51, the upper surface is the same side of the grip holder 20 on which the rotary grip 40 is fitted.

Each switch SW1, SW2, SW3 and the electric circuit can be connected by the wiring for the horn etc. within the steering wheel. The electric circuit includes a horn control relay corresponding to the horn switch SW1, a turning signal control relay corresponding to the turning signal switch SW2, a light control relay corresponding to the light switch SW3, by which relays horns, the turning signals and lights can be controlled.

On the both sides of the switch case 51, extension parts 57 as a connecting member 55 are shaped as one body, the extension parts 57 having fitting projections 56 at a tip thereof. The fitting projections 56 are straight ribs opposed each other, and they are to be removably fitted into fitting recesses (slots) 58 as coupling means of the grip holder 20. These fitting recesses 58 are formed on the both sides of the grip holder 20 in the up-down direction, the surface of which is crossed with the surfaces of the outer periphery and the inner periphery of the grip holder 20. In this case, ribs 28 so as to prevent the switch case 51 from falling downwards are formed along the under edge parts of both sides of the grip holder 20.

In this embodiment, in case a person physically handicapped in the lower limbs is to drive an automobile using the steering wheel rotating apparatus, the shaft 41 of the rotary grip 40 is fitted and pushed into the grip hole 21 of the grip holder 20 which is secured to the steering wheel 11 by the fixing bands 30 and the bolts 33. Thus the rotary grip 40 is rotatably fitted and held the grip holder 20. Further the fitting projections 56 formed in the switch case 51 of the switch unit 50 are fitted into the fitting recesses 58 of the grip holder 20, and the switch unit 50 and the grip holder 20 becomes incorporated, the connector 53 at the tip of the harness 52 is connected to the electric circuit of the automobile. In this condition the horn switch SW1, the turning signal switch SW2 and the light switch SW3 can be operated by the same hand which is gripping the rotary grip 40. In this operating condition the rotary grip 40 is gripped and rotated with one hand (the right hand, for example, in the case of an automobile with a steering wheel on the right side), the steering wheel can be operated the same as ordinarily, and at the same time the horn switch SW1, the turning signal switch SW2 and the light switch SW3 positioned close to the rotary grip 40 can be operated by the finger of the hand gripping the rotary grip 40. Therefore an accelerator and a brake can be operated by the other hand.

In the case a person physically handicapped in one hand, as the horn switch SW1, the turning signal switch SW2 and the light switch SW3 can be operated by one hand gripping the rotary grip 40 at the same time without releasing his hold from the steering wheel, more safety operation can be attained.

When a non-physically handicapped person is to operate the steering wheel, the fitting projections 56 formed in the switch case 51 of the switch unit 50 is taken off from the fitting recesses 58 of the grip holder 20 and the connector 53 at the tip of the harness 52 is taken off. Then, the push button 24 for release from engaging for the rotary grip 40 comes out on the surface of the inner periphery of the grip holder 20, and the shaft 41 of the rotary grip 40 is pulled out while the push button 24 is pushed and the engaging portion 23 is kept back from the inner surface of the grip hole 21 (non-projected condition). In this way only the grip holder 20 is attached to the steering wheel 11, a non-physically handicapped person can operate the steering wheel 11 smoothly.

According to this embodiment, following effects will be obtained.

(1) As the switch unit 50 is removably fitted to the grip holder 20, each of the switch SW1, SW2, and SW3 can be operated by a finger (thumb, for example) of the hand which is gripping the rotary grip 40 being inserted into the grip hole 21 of the grip holder 20. Therefore a person physically handicapped in the lower limbs can operate the steering wheel and the switches for the horn, the turning signal and the light by one hand, and can smoothly operate the accelerator and brake by the other hand. Recently, a lot of automobiles can have a little space between a steering wheel and a dash panel, such the operation lever for the accelerator and brake having the switches as shown in FIG. 9 is rather hard to operate. In this embodiment such a problem will be solved easily.

(2) As the rotary grip 40 and the switch unit 50 are removably fitted to the grip holder 20 without using a tool for fitting, a non-handicapped person operates the automobile without a hitch by removing both the rotary grip 40 and the switch unit 50. Further a risk to operate the switches of the switch unit 50 accidentally can be avoided in case a non-physically handicapped person operates the automobile.

(3) As the switch unite 50 is attached to cover the push button 24 which operates the engaging member 22 for rotary grip 40, an accident such as the push button 24 is imprudently pushed and the rotary grip 40 is come off can be prevented beforehand when the shaft 41 of the rotary grip 40 is inserted to the grip hole 21. Thus reliability for the safe operation can be improved.

Figure 7:
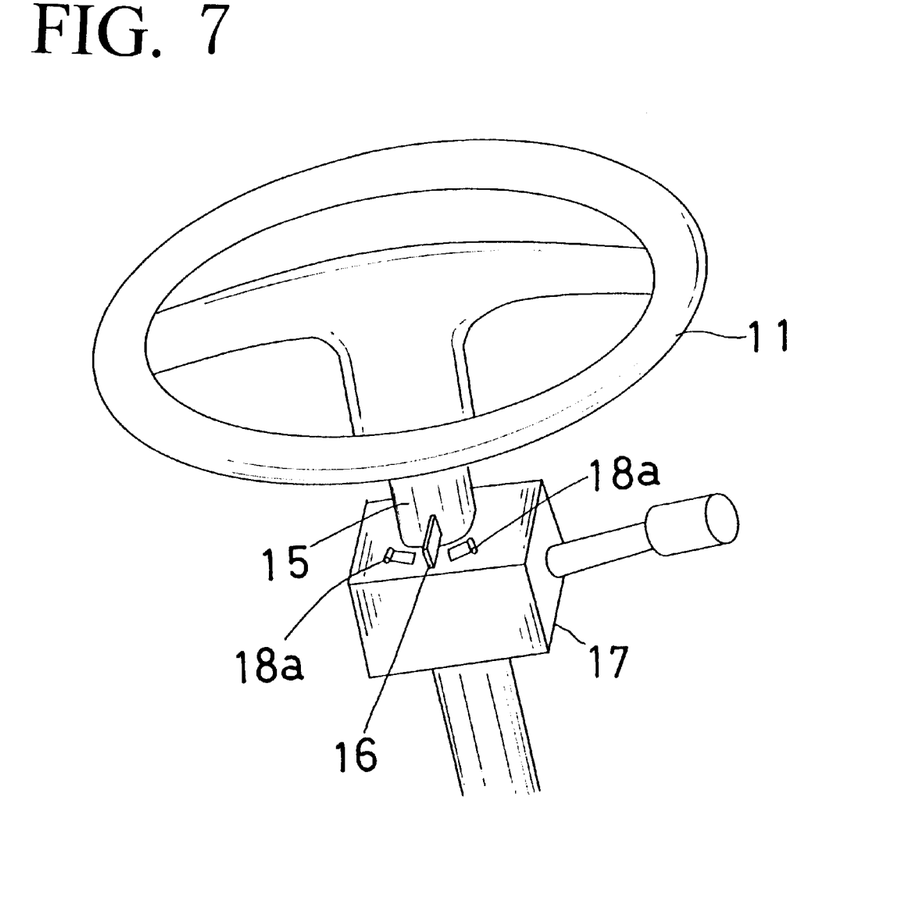
FIG. 7 is a schematic perspective view showing a automatic canceller mechanism of a turning signal which can be added to the embodiment.
Figure 8:
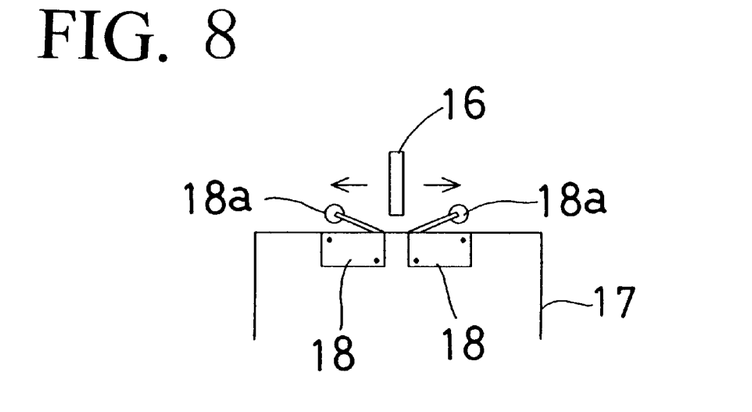
FIG. 8 is a schematic front sectional view of the main part of the automatic canceller mechanism.

FIGS. 7 and 8 show an automatic canceler for the turning signal (winker) which can be added to the above mentioned embodiment. In these FIGS. 7, 8 an operation member 16 is fixed to a rotary shaft 15 of the steering wheel 11, and a pair of operation part 18a of a pair of micro-switch 18 is arranged to the upper surface of a fixed box 17 fixed to the steering column 1. In the fixed box 17, the electrical circuit for the control as mentioned above is stored and a pair of micro-switch 18 is provided to the box. In this case, when the steering wheel is turned left or right for the settled angle (35° for example from the straight ahead state of the steering wheel), the operation member 16 pushes the operation parts 18a of the micro-switches 18 so that the movement of the turning signal can be automatically canceled.

In addition, as for the above embodiment the projections are formed on the switch unit 50 and recesses are formed on the grip holder 20 for the removable connecting means between the switch unit 50 and the grip holder 20. It is no problem if the recesses are formed conversely on the switch unit 50 and the projections are formed on the grip holder 20.

And any of the switch SW1 for the horn, the switch SW2 for the turning signal, and the switch SW3 for the light can be provided to the switch unit 50. But it is more desirable to provide all of the switch SW1 for the horn, the switch SW2 for the turning signal, and the switch SW3 for the light in considering with the better operation. Further it is good to increase a switch for the wiper if necessary.

In the above embodiment the switch SW1 for the horn, the switch SW2 for the turning signal, the switch SW3 for the light are connected by the cable to the electrical circuit for the control with the built-in relay. It is possible that the above electrical circuit is operated by the switch SW1 for the horn, the switch SW2 for the turning signal, and the switch SW3 for the light by wireless, too.

As explained above, according to the steering wheel rotating apparatus for physically handicapped persons of the present invention, the switches for the horn, turning signal, light, wiper and so on can be operated by a thumb or other finger of the hand which is gripping the rotary grip, thus the operator can smoothly operate the apparatus, since the switch unit having the switch case and at least one switch provided thereon is detachably fitted to the grip holder.

As the rotary grip and the switch unit are removably fitted to the grip holder, a non-handicapped person operates the automobile without a hitch by removing both the rotary grip and the switch unit beforehand. Further a risk to operate the switches of the switch unit accidentally can be eliminated in case a non-physically handicapped person operates the automobile and reliability of operation is improved.

What is claimed is:

1. A steering wheel rotating apparatus for physically handicapped persons, the apparatus comprising:

a grip holder having a grip hole and means for attaching the grip holder to a steering wheel of an automobile;

a rotary grip having a shaft with an insertion part detachably received in the grip hole and a grip body part mounted on the shaft, the shaft having a partly narrowed engaging portion in the insertion part;

an engaging member supported by the grip holder and having a movable portion supported for movement between a first position in which the movable portion projects into the grip hole and engages the engaging portion of the shaft and prevents the shaft from being removed from the grip hole, and a second position in which the movable portion is disengaged from the engaging portion, biasing means biasing the movable portion of the engaging member toward the first position, and an operating portion for moving the movable portion between the first and second positions; and a switch unit detachably fittable to the grip holder, covering the operating portion of the engaging member and having a switch case and at least one switch on the switch case.

2. The steering wheel rotating apparatus according to claim 1 wherein the switch unit includes at least one of a switch for a horn, a switch for a turning signal, a switch for a light, and a switch for a wiper.

* * * * *